(12) United States Patent
Leighton

(10) Patent No.: US 8,765,694 B2
(45) Date of Patent: Jul. 1, 2014

(54) METHOD FOR TREATING OBESITY

(71) Applicant: Rhamnopharma Inc., Oakland, CA (US)

(72) Inventor: Anton Leighton, Oakland, CA (US)

(73) Assignee: Rhamnopharma Inc., Oakland, CA (US)

( * ) Notice: Subject to any disclaimer, the term of this patent is extended or adjusted under 35 U.S.C. 154(b) by 0 days.

(21) Appl. No.: 13/946,931

(22) Filed: Jul. 19, 2013

(65) Prior Publication Data

US 2013/0310330 A1 Nov. 21, 2013

Related U.S. Application Data

(63) Continuation of application No. PCT/US2012/043075, filed on Jun. 19, 2012.

(60) Provisional application No. 61/499,638, filed on Jun. 21, 2011, provisional application No. 61/515,806, filed on Aug. 5, 2011, provisional application No. 61/641,117, filed on May 1, 2012.

(51) Int. Cl.
| | | |
|---|---|---|
| *A01N 43/04* | (2006.01) | |
| *A61K 31/70* | (2006.01) | |
| *A61K 31/715* | (2006.01) | |

(52) U.S. Cl.
USPC .............................................. 514/25; 514/53

(58) Field of Classification Search
CPC .................................................. A61K 31/7028
USPC ...................................................... 514/25, 53
See application file for complete search history.

(56) References Cited

U.S. PATENT DOCUMENTS

| | | |
|---|---|---|
| 5,455,232 A | 10/1995 | Piljac et al. |
| 5,514,661 A | 5/1996 | Piljac et al. |
| 2006/0062863 A1 | 3/2006 | Ghosal |
| 2006/0100172 A1 | 5/2006 | Monsan et al. |
| 2009/0220603 A1 | 9/2009 | Piljac et al. |
| 2011/0257115 A1 | 10/2011 | Leighton |

FOREIGN PATENT DOCUMENTS

WO  WO 2011/109200 A2  9/2011

OTHER PUBLICATIONS

Stipcevic, T., Piljac, A., Piljac, G. (2006) Enhanced healing of full-thickness burn wounds using di-rhamnolipid. Burns, vol. 32, No. 1, p. 24-34.*
Hawa, M.I., Thivolet, C., Mauricio, D., Alemanno, I., Cipponeri, E., Collier, D., Hunter, S., Buzzetti, R., De Leiva, A., Pozzilli, P., Gelsie, R.D.G. (2009) Metabolic Syndrome and Autoimmune Diabetes: Action LADA 3. Diabetes Care, vol. 32, No. 1, p. 160-164.*
Abdel-Mawgoud, A.M., Lépine, F., Déziel, E. (2010) Rhamnolipids: diversity of structures, microbial origins and roles. Applied Microbiology and Biotechnology, vol. 86, p. 1323-1336.*
International Search Report and Written Opinion of PCT Application No. PCT/US2012/043075 mailed Feb. 13, 2013.

* cited by examiner

*Primary Examiner* — Scarlett Goon
(74) *Attorney, Agent, or Firm* — Perkins Coie LLP; Viola T. Kung

(57) ABSTRACT

The present invention is directed to methods for treating obesity, reducing excessive body weight, treating an obesity-related condition, treating unwanted localized fat deposits, and treating areas of cellulite. The method comprises the steps of first identifying a subject in need thereof, and administering to the subject an effective amount of rhamnolipids. A pharmaceutical composition comprising rhamnolipids can be applied by any accepted mode of administration including oral, intranasal, subcutaneous, percutaneous, intravenous, or intracutaneous administration.

8 Claims, 7 Drawing Sheets

METHOD FOR TREATING OBESITY

This application is a continuation of PCT/US2012/043075, filed Jun. 19, 2012, which claims the benefit of U.S. Provisional Application Nos. 61/499,638, filed Jun. 21, 2011, 61/515,806, filed Aug. 5, 2011 and 61/641,117, filed May 1, 2012. The contents of the above-identified applications are incorporated herein by reference in their entirety.

FIELD OF THE INVENTION

The present invention relates to using rhamnolipids for treating obesity and obesity-related conditions such as metabolic syndrome, hypertension, type 2 diabetes, non-alcoholic fatty liver disease or obesity-related kidney disease.

BACKGROUND OF THE INVENTION

Obesity is a medical condition in which excess body fat has accumulated to the extent that it may have an adverse effect on health, leading to reduced life expectancy and/or increased health problems. Body mass index (BMI), a measurement which compares weight and height, defines individuals as overweight or as suffering from excessive body weight (pre-obese) if their BMI is between 25 and 30 kg/m$^2$, and overtly obese when their BMI is greater than 30 kg/m$^2$. There is increased risk of co-morbidities for individuals with a BMI between 25.0 to 29.9, and moderate to severe risk of co-morbidities for individuals with a BMI greater than 30. Obesity is a serious health and economic burden, and predisposes an individual to a variety of cardiometabolic diseases. Obesity increases the likelihood of metabolic syndrome, hypertension, type 2 diabetes, non-alcoholic fatty liver disease, or obesity-related kidney disease.

Metabolic syndrome is characterized by the presence of three or more of the following components: abdominal obesity (waist circumference >102 cm in men, >88 cm in women), elevated triglycerides (>150 mg/dl or on drug treatment for elevated triglycerides), reduced HDL-C level (<40 mg/dl in men, <50 mg/dl in women or on drug treatment for reduced HDL-C), hypertension (systolic blood pressure >130 mmHg or diastolic blood pressure >85 mm Hg or on antihypertensive drug treatment) and impaired fasting glucose (100-125 mg/dl or on anti-diabetic drug treatment).

Hypertension is a chronic medical condition in which the blood pressure in the vasculature is elevated. This requires the heart to work harder than normal to circulate blood through the blood vessels. Hypertension is present if it is persistently at or above 140/90 mmHg. According to population studies, almost two-thirds of people suffering from obesity are at risk of hypertension.

Diabetes mellitus type 2 (type 2 diabetes) is a metabolic disorder that is characterized by high blood glucose in the context of insulin resistance and relative insulin deficiency. Obesity is thought to be the primary cause of type 2 diabetes in those people who are genetically predisposed to the disease. Long-term complications from high blood sugar can include heart disease, strokes, diabetic retinopathy where eyesight is affected, kidney failure, and poor circulation of limbs leading to amputations.

Non-alcoholic fatty liver disease includes fatty liver (accumulation of fat in the liver), non-alcoholic steatohepatitis (fat in the liver causing liver inflammation), and often leads to cirrhosis (irreversible, advanced scarring of the liver as a result of chronic inflammation of the liver). All of the stages of non-alcoholic fatty liver disease are now believed to be due to insulin resistance, a condition closely associated with obesity. Moreover, studies demonstrate a correlation between BMI and the degree of liver damage in non-alcoholic fatty liver disease, which shows that the greater the BMI, the greater the liver damage. Non-alcoholic fatty liver disease is an increasingly common liver disease in developed countries because of the rising prevalence of obesity. Elevated transaminases, alanine transaminase (ALT) and aspartate transaminase (AST), are used to monitor non-alcoholic fatty liver disease in obese patients.

Obesity can indirectly influence kidney disease by increasing rates of diabetes and hypertension, which are known risk factors for kidney disease. However, there is growing evidence that obesity per se, even in the absence of diabetes, significantly increases the risk of obesity-related kidney disease and adversely impacts its progression. Obesity-related kidney disease is characterized by albuminuria, glomerulomegaly and secondary focal glomerulosclerosis. Glomerulosclerosis refers to a scarring of the kidneys' tiny blood vessels, the glomeruli, which are the functional units in the kidney that filter urine from the blood. Weight loss, blockade of the renin angiotensin system, and restoration of adipokine levels may be beneficial to ameliorate the progression of obesity-related kidney disease.

Obese Zucker rats (OZRs) have defective brain leptin dependent signal transduction, resulting in markedly increased food intake and decreased energy expenditure. They are used as an animal model of hyperphagia, obesity and associated hyperlipidemia, insulin resistance, fatty liver disease, and renal disease. OZRs are hyperphagic, hyperlipidemic, hyperinsulinemic, and have severe peripheral insulin resistance, metabolic characteristics also seen in human patients with type 2 diabetes and metabolic syndrome. These changes develop during the first 20 weeks of life. OZRs typically die of renal failure, specifically from a glomerular disease pathologically similar to human focal segmental glomerulosclerosis. Various experimental maneuvers have been found to attenuate the development of glomerular disease in OZRs, including treatment with lipid-lowering agents, ovariectomy, and reduction of food intake (Stevenson, F. T., et al., Obesity Research (2001) 9:492-499; Koteish, A., Diehl, A. M., Liver Dis (2001) 21:89-104).

Obesity is often accompanied by excess fat storage in tissues other than adipose tissue, including liver and skeletal muscle, which may lead to local insulin resistance and may stimulate inflammation, as in steatohepatitis. In addition, obesity changes the morphology and composition of adipose tissue, leading to changes in protein production and secretion. Some of these secreted proteins, including several pro-inflammatory mediators, may be produced by macrophages resident in the adipose tissue. The changes in inflammatory status of adipose tissue and liver with obesity feed a growing recognition that obesity represents a state of chronic low-level inflammation.

Adipose tissue has a primary role in the pathogenesis of non-alcoholic fatty liver disease (NAFLD) and non-alcoholic steatohepatitis (NASH), namely the central (or upper body) obesity phenotype associated with increased visceral fat. Studies have shown that the amount of intra-hepatocellular lipids increases by approximately 20% for any 1% increase in total or subcutaneous adipose tissue, but doubles for any 1% increase in intra-abdominal adipose tissue. Therefore, even modest increases in visceral fat (in the absence of increased body mass index (BMI)) may cause steatosis (Bugianesi E., et al., Diabetologia (2005) 48:634-642).

Lipomas are adipose tissue tumors, which are benign, slow-growing tumors composed of enlarged adipose tissue cells, preferentially in subcutaneous tissue. They can become painful and the compression derived therefrom on blood vessels may cause neuralgia. Subcutaneous accumulations of fat or proliferations of adipose cells such as lipomas or lipedemas are predominantly treated by surgical means through liposuction or direct surgical removal. Treatment measures of these types are associated with the known complications or risks caused by anesthesia, local reactions and possible infections, and in some circumstances, require admission to a hospital ward. There are currently no FDA-approved injections for the reduction or elimination of local unwanted body fat.

Cellulite is a skin alteration often described as an "orange peel," "mattress" or "dimpling" appearance on the thighs, buttocks and sometimes lower abdomen and upper arms of otherwise healthy women. Cellulite is caused by small protrusions of fat called papillae adiposae into the dermis. This structural alteration of subcutaneous fat protruding (or herniating) into the dermis gives skin the bumpy appearance referred to as cellulite. Individuals with cellulite and higher BMIs have a weaker, less dense connective tissue structure, leading to increased extrusion of adipose tissue lobules through the hypodermis. These individuals have a higher amount of extrusion of adipose tissue while the thickness of the dermis is significantly lower. Affected individuals with lower BMIs show differences in the thickness of the adipose tissue layer, with a significantly thicker adipose layer in individuals with clinically evident cellulite.

SUMMARY OF THE INVENTION

The present invention is directed to a method for reducing excessive body weight from a subject. The method comprises the steps of identifying a subject suffering from excessive weight or overt obesity, and administering to the subject an effective amount of rhamnolipids.

The present invention is also directed to a method for treating an obesity-related condition in a subject. The method comprises the steps of first identifying a subject suffering from (i) excessive body weight or overt obesity, and (ii) an obesity-related condition, and administering to the subject an effective amount of rhamnolipid, wherein said obesity-related condition is metabolic syndrome, hypertension, type 2 diabetes, non-alcoholic fatty liver disease, or obesity-related kidney disease.

The present invention is further directed to a method for treating unwanted localized fat deposits in a subject. The method comprises the steps of first identifying a subject suffering from localized fat deposits and administering into or around the areas of localized fat deposits of the subject an effective amount of rhamnolipids, whereby the local fat deposits are reduced.

The present invention is further directed to a method for treating areas of cellulite in a human subject. The method comprises the steps of first identifying a human subject suffering from cellulite and administering into or around the areas of cellulite an effective amount of rhamnolipids, whereby the appearance of cellulite is improved.

The pharmaceutical composition comprising the active compound can be applied by any accepted mode of administration including oral, intranasal, subcutaneous, percutaneous, intravenous, or intracutaneous administration. Subcutaneous administration is preferred.

Figure 1:
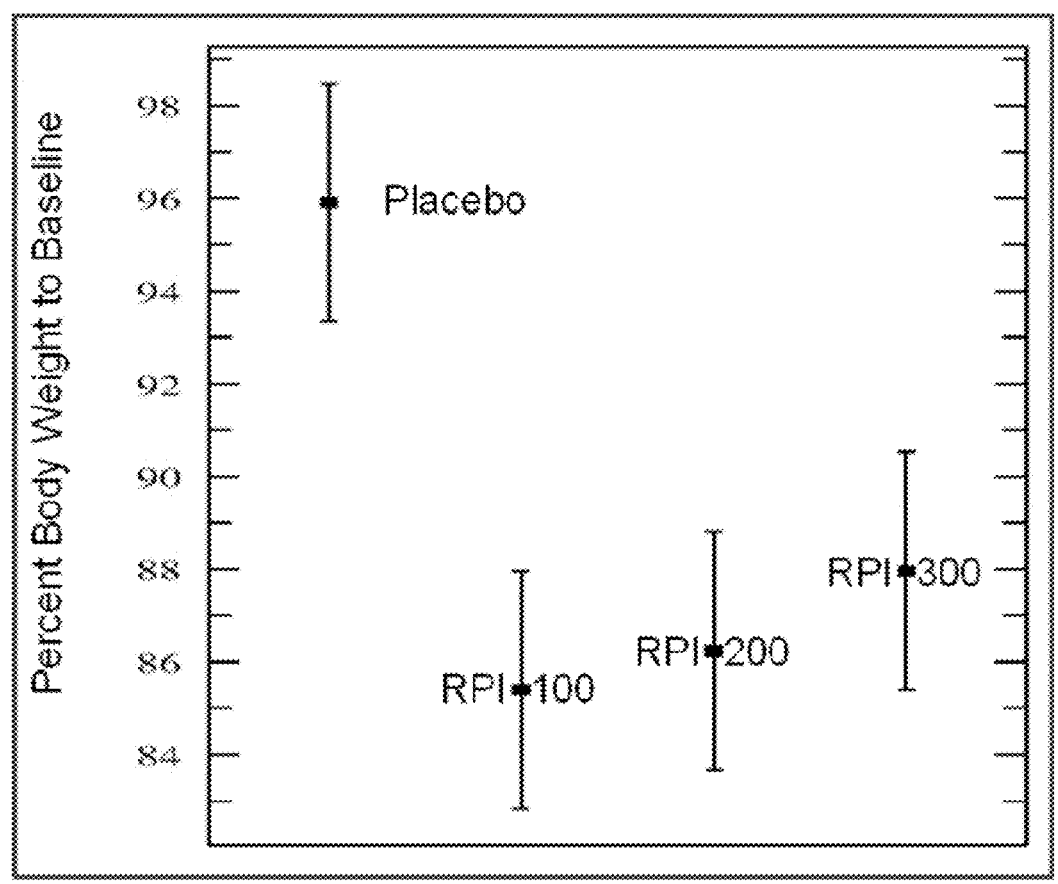
FIG. 1 shows the plotted ANOVA results from an analysis comparing the proportion of the difference of post-treatment to pre-treatment body weights of groups of mice treated with RPI-100, RPI-200, RPI-300, and the placebo. Error bars represent the 95% confidence intervals for each group.

Error bars in FIGS. 3-6 and 8-10 represent the 95% confidence intervals for each group.

DETAILED DESCRIPTION OF THE INVENTION

The inventor has discovered that rhamnolipids are effective for reducing excessive body weight, treating obesity-related conditions such as metabolic syndrome, hypertension, type 2 diabetes, non-alcohol fatty liver disease, or obesity-related kidney disease, removing unwanted localized fat deposits, and treating cellulite areas in a subject. By administering rhamnolipids to a subject, the subject's condition or disorder is improved.

Rhamnolipids

Rhamnolipids are biosurfactants containing rhamnose sugar molecules and βhydroxyalkanoic acids. Rhamnolipids suitable to be used in the present invention include natural rhamnolipids, for example, obtained from *Pseudomonas aeruginosa*; rhamnolipids produced by any Pseudomonad, including *P. chlororaphis, Burkholderia pseudomallei, Burkholdera (Pseudomonas) plantarii*, and any recombinant Pseudomonad. Suitable rhamnolipids also include those produced by other bacteria or by plants either naturally or through (genetic) manipulation. Suitable rhamnolipids further include rhamnolipids and their analogs prepared by chemical synthesis or expression by mammalian cells. Suitable rhamnolipids include those disclosed in U.S. Pat. Nos. 7,262,171 and 5,514,661, in which the structures of rhamnolipids are incorporated herein by reference.

Suitable rhamnolipid formulations contain one or more rhamnolipids of formula (I)

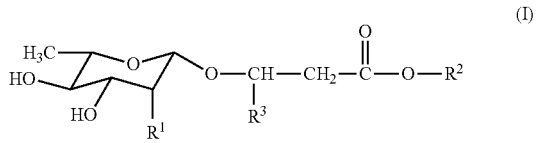

(I)

wherein:

$R^1$=H, unsubstituted α-L-rhamnopyranosyl, α-L-rhamnopyranosyl substituted at the 2 position with a group of formula —O—C(=O)—CH=CH—$R^5$, or —O—C(=O)—CH=CH—$R^5$;

$R^2$=H, $C_{1-6}$alkyl, —$CHR^4$—$CH_2$—COOH or —$CHR^4$—$CH_2$—$COOR^6$; and $R^3$-$R^6$ are independently alkyl.

"Alkyl" refers to groups of from 1 to 12 carbon atoms, either straight chained or branched, preferably from 1 to 8 carbon atoms, and more preferably 1 to 6 carbon atoms.

In one embodiment, $R^3$=—$(CH_2)_x$—$CH_3$, wherein x=4-19; $R^4$=—$(CH_2)_y$—$CH_3$, wherein y=1-19; $R^5$=—$(CH_2)_z$—$CH_3$, wherein z=1-12; and $R^6$=—$C_{1-6}$alkyl, Useful rhamnolipids of the Formula 1 include α-rhamnopyranosyl-(1,2)-α-L-ramnopyranosyl)-3-hydroxydecanoyl-3-hydroxydecanoic acid and has the following structure (Formula 2):

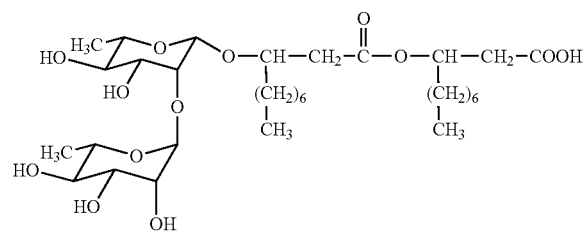

Formula 2

In one embodiment, $R^1$=α-L-rhamnopyranosyl substituted at the 2-position by —O—C(=O)—CH=CH—$R^5$, $R^2$=—$CHR^4$—$CH_2$—COOH, $R^3$=—$(CH_2)_5$—$CH_3$, $R^4$=—$(CH_2)_2$—$CH_3$, and $R^5$=—$(CH_2)_5$—$CH_3$.

In another embodiment, $R^1$=α-L-rhamnopyranosyl substituted at the 2-position by —O—C(=O)—CH=CH—$R^5$, $R^2$=—$CHR^4$—$CH_2$—COOH, $R^3$=—$(CH_2)_5$—$CH_3$, $R^4$=—$(CH_2)_5$—$CH_3$, and $R^5$=—$(CH_2)_5$—$CH_3$;

In another embodiment, $R^1$=α-L-rhamnopyranosyl substituted at the 2-position by —O—C(=O)—CH=CH—$R^5$, $R^2$=—$CHR^4$—$CH_2$—$COOCH_3$, $R^3$=—$(CH_2)_5$—$CH_3$, $R^4$=—$(CH_2)_2$—$CH_3$, and $R^5$, —$(CH_2)_5$—$CH_3$.

Preferred rhamnolipids are L-rhamnosyl-β-hydroxydecanoyl-β-hydroxydecanoate (rhamnolipids 1, Rha-C10-C10) and L-rhamnosyl-L-rhamnosyl-β-hydroxydecanoyl-β-hydroxydecanoate (rhamnolipids 2, Rha-Rha-C10-C10), and the mixture thereof.

Some common di-rhamnolipids useful for this invention include: L-rhamnopyranosyl-L-rhamnopyranosyl-beta-hydroxydecanoyl-beta-hydroxydodecanoate (often referred to as Rha-Rha-C10-C12); L-rhamnopyranosyl-L-rhamnopyranosyl-beta-hydroxytetradecanoyl-beta-hydroxytetradecanoate (often referred to as Rha-Rha-C14-C14).

Pharmaceutical Compositions

One or more rhamnolipids, which are the active ingredient of the present invention, can be used directly as a pharmaceutical composition. One or more rhamnolipids can also be formulated in a pharmaceutical composition which comprises rhamnolipids and one or more pharmaceutically acceptable carriers. The pharmaceutical composition can be in the form of a liquid, a solid, or a semi-solid.

Pharmaceutically acceptable carriers can be selected by those skilled in the art using conventional criteria. Pharmaceutically acceptable carriers include, but are not limited to, sterile water or saline solution, aqueous electrolyte solutions, isotonicity modifiers, water polyethers such as polyethylene glycol, polyvinyls such as polyvinyl alcohol and povidone, cellulose derivatives such as methylcellulose and hydroxypropyl methylcellulose, polymers of acrylic acid such as carboxypolymethylene gel, nanoparticles, polysaccharides such as dextrans, and glycosaminoglycans such as sodium hyaluronate and salts such as sodium chloride and potassium chloride.

In one embodiment, the pharmaceutical composition contains rhamnolipid(s) and a pharmaceutically acceptable carrier in a liquid form. The concentration of rhamnolipid(s) in a liquid pharmaceutical composition is in general about 0.005-20% (w/w), or 0.02-5%, or 0.1-5%, or 0.2 to 5%, or 0.2-2%, or 0.05-0.5% (w/w). In one embodiment, the concentration of rhamnolipid(s) is about 0.2-2%, for example, 0.5% (w/w). In another embodiment, the concentration is about 10-20%, for example, about 15%. "About" as used herein, refers to ±10% of the recited value. The concentration can be higher or lower as long as it delivers an effective and tolerable dose per dosing interval.

In one embodiment, the pharmaceutical composition of the present invention provides an aqueous solution comprising water and rhamnolipids; the composition optionally comprises suitable ionic or non-ionic tonicity modifiers, suitable buffering agents, and rhamnolipids. In one embodiment, the rhamnolipid is at 0.005-20% (w/w), and the aqueous solution has a tonicity of 200-400 mOsm/kG and a pH of 4-9.

The pharmaceutical composition is preferably formulated to have a pH between 4.5-8, more preferably 5-7.4. The pharmaceutical composition may optionally contain a buffer to facilitate a stable pH of 5-7.4.

The pharmaceutical composition optionally contains non-ionic tonicity agents such as mannitol, sucrose, dextrose, glycerol, polyethylene glycol, propylene glycol, or ionic tonicity agent such as sodium chloride. The pharmaceutical composition can further contain ionic or non-ionic surfactants, bile salts, phospholipids, cyclodextrins, micelles, liposomes, emulsions, polymeric microspheres, nanoparticles, other biodegradable microsphere technology, or their combination.

In one embodiment, the pharmaceutical composition is in a dosage form such as tablets, capsules, granules, fine granules, powders, syrups, suppositories, injectable solutions, or the like. The above pharmaceutical composition can be prepared by conventional methods.

For example, a tablet formulation or a capsule formulation may contain other excipients that have no bioactivity and no reaction with rhamnolipids. Excipients of a tablet may include fillers, binders, lubricants and glidants, disintegrators, wetting agents, and release rate modifiers. Binders promote the adhesion of particles of the formulation and are important for a tablet formulation. Examples of binders include, but not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone. A tablet formulation may contain 1-90% of rhamnolipids. A capsule formulation may contain 1-100% of rhamnolipids.

In one embodiment, the pharmaceutical composition comprises one or more rhamnolipids, a serum albumin, and a pharmaceutically acceptable carrier. In this pharmaceutical composition, a majority of the rhamnolipids are non-covalently bound to the fatty acid binding sites of albumin or to other binding sites of albumin. Albumin bound rhamnolipids prolong the beneficial effects of rhamnolipids so that longer dosing intervals can be used.

In another embodiment, the pharmaceutical composition comprises one or more rhamnolipids imbedded in a solid or semi-solid matrix, and is in a liquid, solid, or semi-solid form. The pharmaceutical composition can be injected subcutaneously to a subject and then the active ingredients slowly released in the subject. The formulation may contain 1-90% rhamnolipids.

The pharmaceutical composition is preferred to be stable at room temperature for at least 6 months, 12 months, preferably 24 months, and more preferably 36 months. Stability, as used herein, means that rhamnolipid maintains at least 80%, preferably 85%, 90%, or 95% of its initial activity value.

The pharmaceutical compositions of the present invention can be prepared by aseptic technique. The purity levels of all materials used in the preparation preferably exceed 90%.

Methods of Use

The present invention is directed to a method for reducing excessive body weight from a subject. The method comprises the steps of identifying a subject suffering from excessive weight or overt obesity, and administering to the subject an effective amount of rhamnolipids. A human subject suffering from excessive body weight (pre-obese) is defined by a Body Mass Index (BMI) between 25 and 30 $kg/m^2$ and a human subject suffering from overt obesity is defined by BMI greater than 30 $kg/m^2$. Rhamnolipids effectively reduce excessive body weight of a pre-obese subject or an overtly obese subject.

The present invention is also directed to a method for treating obesity. The method comprises the steps of identifying a subject suffering from overt obesity, and administering to the subject an effective amount of rhamnolipids, whereby the excessive body weight of the subject is reduced.

The present invention is directed to a method for treating an obesity-related condition in a subject. The method comprises the steps of first identifying a subject suffering from (i) excessive body weight or overt obesity, and (ii) an obesity-related condition, and administering to the subject an effective amount of rhamnolipid, wherein said obesity-related condition is metabolic syndrome, hypertension, type 2 diabetes, non-alcoholic fatty liver disease, or obesity-related kidney disease.

In one embodiment, the method reduces or alleviates the symptoms of an obesity-related condition, metabolic syndrome. The present invention provides a method to treat metabolic syndrome characterized by central obesity; fasting hyperglycemia, which includes type 2 diabetes, impaired glucose tolerance or insulin resistance; elevated blood pressure, triglyceride, cholesterol, and blood glucose levels. The present invention is effective in reducing body weight, blood pressure, and triglyceride, cholesterol, and blood glucose levels.

In another embodiment, the method reduces or alleviates the symptoms of an obesity-related condition, hypertension. The present invention provides a method to treat hypertension characterized by truncal obesity and elevated blood pressure. The present method reduces elevated blood pressure.

In another embodiment, the method reduces or alleviates the symptoms of an obesity-related condition, type 2 diabetes. The present invention provides a method to treat type 2 diabetes characterized by insulin resistance, where the fat, liver, and muscle cells do not respond correctly to insulin, and as a result, blood sugar does not get stored in these cells for energy. Type 2 diabetes is most often characterized by a BMI >25 $kg/m^2$ and increased levels of blood glucose compared with normal subjects. The present invention effectively reduces body weight and blood glucose levels in subjects with type 2 diabetes.

In another embodiment, the method reduces or alleviates the symptoms of an obesity-related condition, non-alcoholic fatty liver disease. The present invention provides a method to treat non-alcoholic fatty liver disease characterized by fat deposited in the liver not due to excessive alcohol use, obesity and elevated liver transaminase levels, specifically alanine aminotransaminases (ALT). The present invention is effective in decreasing body weight and liver transaminase (ALT) levels.

In another embodiment, the method reduces or alleviates the symptoms of an obesity-related condition, obesity-related kidney disease. The present invention provides a method to treat obesity-related kidney disease characterized by damage to the renal glomeruli and an increase in creatinine levels. For example, the method is effective to treat glomerulosclerosis, which is characterized by scarring of the kidney's glomeruli, obesity, and elevated creatinine levels. The present invention effectively reduces body weight and creatinine levels.

The present invention is directed to a method for treating unwanted localized fat deposits in a subject. The method comprises the steps of first identifying a subject suffering from localized fat deposits and administering into or around the areas of localized fat deposits of the subject an effective amount of rhamnolipids, whereby the local fat deposits are reduced.

In one embodiment, the method reduces unwanted localized fat deposits. The present invention provides a method to treat unwanted localized fat deposits characterized by excess subcutaneous adipose tissue. The present invention effectively reduces unwanted subcutaneous adipose tissue.

In one embodiment, the method reduces unwanted localized fat from a subject suffering from lipodystrophy, which is characterized by abnormal conditions of the subject's adipose tissue. Examples of lipodystrophy include, but are not limited to lipodystrophy caused by metabolic abnormalities due to genetic issues, which are characterized by insulin resistance and are associated with metabolic syndrome; and HIV-associated lipodystrophy, as characterized by the presence of an enlarged dorsocervical fat pad, circumferential expansion of the neck, breast enlargement, and/or abdominal visceral fat accumulation.

In another embodiment, the method reduces unwanted localized fat from a subject suffering from lipoma, which is characterized by a benign tumor of adipose subcutaneous tissue.

The present invention is directed to a method for treating areas of cellulite in a human subject. The method comprises the steps of first identifying a human subject suffering from cellulite and administering into or around the areas of cellulite an effective amount of rhamnolipids, whereby the appearance of cellulite is improved. The present invention provides a method to treat cellulite characterized by a modification of skin topography evident by skin dimpling and nodularity that is caused by the protrusion of subcutaneous fat within fibrous connective tissue, leading to a padded or orange peel-like appearance.

In the above treatment methods, rhamnolipids can be the only active ingredient in a treatment method, or rhamnolipids can be used together with another active ingredient that is useful for the treatment.

"An effective amount," as referred to in the above methods, is the amount effective to treat a disease by ameliorating the condition or reducing the symptoms of the disease.

The pharmaceutical composition of the present invention can be applied by systemic administration. Systemic administration includes oral, intranasal, subcutaneous, percutaneous, or intravenous administration, and other systemic routes of administration, e.g., intracutaneous injection. Subcutaneous administration is the preferred route of administration for the present invention. Intracutaneous injection can be used for reducing areas of cellulite.

In one embodiment, the pharmaceutical composition is applied 1-3 times daily, 1-2 times daily, once daily, once every 2-3 days, once weekly, once every 2 weeks, once every 4 weeks, or once every one to three months by intranasal, intravenous, subcutaneous, percutaneous, or intracutaneous administration.

In one embodiment, the pharmaceutical composition is an oral formulation that is taken 1-4 times daily, once every 2-3 days, once weekly, once every 2 weeks, or once every 4 weeks.

In another embodiment, the pharmaceutical composition is a delayed release formulation injected intracutaneously.

Those of skill in the art will recognize that a wide variety of delivery mechanisms are also suitable for the present invention.

The present invention is useful in treating a mammalian subject, such as humans, dogs and cats. The present invention is particularly useful in treating humans.

The following examples further illustrate the present invention. These examples are intended merely to be illustrative of the present invention and are not to be construed as being limiting.

EXAMPLES

Example 1

Objective

Originally, the objective of this study was to determine the effects of treatment with three different pharmaceutical formulations of rhamnolipids within the context of an allergic rhinitis study in mice. However, the weight loss effects due to treatment with the various rhamnolipids were unexpectedly discovered during the course of this study.

Materials
Animal:
Balb/C mice were used in this study and were eight weeks old. The treatment groups and the placebo group were each composed of 10 mice. Allergenization was performed in a similar fashion as reported in the literature.
Sensitization Materials:
The following were used to sensitize and induce allergic rhinitis in the mice:
1. OVA/Alum (0.8 µg and 0.8 mg/mouse, respectively) was used as an intraperitoneal injection. Grade V OVA was from Sigma-Aldrich (St. Louis, Mo.). Alum was aluminum hydroxide gel from Pierce Biotechnology (Rockford, Ill.); now Thermo Fisher Scientific, Inc.)
2. An ovalbumin (OVA) solution (5 µL of 50 mg/ml of stock OVA solution in 1×PBS) was administered intranasally.

Rhamnolipid Mixtures:
1. RPI-100: JBL515 was supplied by Jeneil Biotech (Saukville, Wis.) as a 15% solution of a rhamnolipid mixture of a combination of mono-Rhamnolipid (Rha-$C_{10}$-$C_{10}$) and di-Rhamnolipid (Rha-Rha-$C_{10}$-$C_{10}$) consisting at a ratio of approximately 1:1.21, respectively.

The 15% solution was diluted in 0.95% saline to prepare a dosing solution of 0.5%.

2. RPI-200: JBR8% was supplied by Jeneil Biotech (Saukville, Wis.) as an 8% solution of a mono-Rhamnolipid (Rha-$C_{10}$-$C_{10}$).

The 8% solution was diluted in 0.95% saline to prepare a dosing solution of 0.5%.

3. RPI-300: KIT was supplied by Karlsruher Institut für Technologie (KIT) (Karlsruhe, Germany) as a powder of di-Rhamnolipid (Rha-Rha-$C_{10}$-$C_{10}$).

The powder was reconstituted in 0.95% saline (5 mg/ml) to prepare a dosing solution of 0.5%.

Saline was used as the placebo in this study.
Methods
Mice were sensitized once-weekly with four intraperitoneal injections of OVA/Alum (Day 0, 5, 14 and 21). From Day 22-39, anesthetized mice were administered once-daily doses of the OVA stock solution instilled in each nostril.

On Day 37, mice were assigned to one of three rhamnolipid treatment groups or a placebo group. The rhamnolipid treatment groups received a rhamnolipid mixture containing RPI-100, RPI-200, or RPI-300. The mice in each treatment group received 5 µl of the designated 0.5% rhamnolipid mixture in saline per nostril at two different time points on Day 37, for a total applied volume of 20 µl. Whereas, the mice in the placebo group received 5 µl of normal saline per nostril at the same two different time points on Day 37, for a total applied volume of 20 µl. The doses were administered 3 hours and 2 hours prior to the intranasal dose of the OVA solution. Body weights of the mice were measured and recorded on Days 35, 37, and 39 as part of a standard animal safety observation protocol.

Results
Post-Treatment with Intranasal Doses of Rhamnolipids
Gross body weight differences were observed 2 days post-treatment (Day 39) when compared with 2 days pre-treatment (Day 35) body weight measurements. A formal statistical analysis was performed using an analysis of variance (ANOVA) (www.physics.csbsju.edu) to compare the proportion of the difference of post-treatment to pre-treatment body weights of the respective treatment groups and the placebo group. All four groups, including the groups of mice treated with RPI-100, RPI-200, RPI-300, and the placebo group, were included in the ANOVA. The probability of the ANOVA result, assuming the null hypothesis, was less than 0.0001. The data were presented graphically with error bars representing the 95% confidence intervals (CI) of each group (FIG. 1). Thus, these results show that there was a statistically significant reduction in body weight in the mice treated with rhamnolipids when compared to those mice treated with the placebo.

Conclusions:
The results of this study demonstrate that intranasal administration of three different formulations of rhamnolipids was effective in eliciting weight loss in normal weight mice. Specifically, treatment of mice with mono-rhamnolipid, di-rhamnolipid, or a combination of both mono-rhamnolipid and di-rhamnolipid resulted in a statistically significant reduction of body weight when compared to those mice treated with the placebo.

Example 2

Objective

The objective of this study was to explore the effects and feasibility of subcutaneous injections of rhamnolipids at varying concentrations in a human model.

Materials

Subject:

Human subject: 60 year old male, 108 kg (BMI 29.8) with known hypertension.

Injections:

Standard insulin syringes (Monoject®) were used for injections.

Rhamnolipids:

15% (w/v) solution of rhamnolipid: JBL515 was used for the 15% solution of rhamnolipid.

1, 2.5, 5, and 10% (w/v) solution of rhamnolipid: Each solution was prepared by diluting JBL515 (15%) in water.

Methods and Results

Study Part A: Initial Study of Small, Increasing Doses of Rhamnolipid Injections The subject injected himself with initial small test doses of approximately 0.5 ml of a 1% solution of rhamnolipids into subcutaneous fatty tissue located in his left lumbar region and his right iliac region.

As these initial injections were extremely well tolerated with no signs of significant inflammation, a subsequent test was performed to determine the potential effects of increasing concentrations of rhamnolipid injections. The subject injected himself with incrementally increasing concentrations of rhamnolipid injections into the subcutaneous area of his right lumbar region of his anterior abdomen and left iliac region every other day beginning on Day 1 and ending on Day 9 (Table 1). A transient hardening of the injected subcutaneous fatty tissue along with a subsequent reduction in overall volume of the underlying fatty tissues was observed over the next 10 days post-injection.

TABLE 1

Study Part A: Administration of Increasing Concentrations of Rhamnolipids

|  | Day 1 | Day 3 | Day 5 | Day 7 | Day 9 |
| --- | --- | --- | --- | --- | --- |
| % Solution of rhamnolipid | 1% | 2.5% | 5% | 10% | 15% |
| # of injections | 1 | 2 | 2 | 2 | 2 |
| Volume of each injection | 0.5 ml | 0.5 ml | 0.5 ml | 0.5 ml | 0.5 ml |
| Total volume and % of rhamnolipid administered per day | 0.5 ml of 1% | 1.0 ml of 2.5% | 1.0 ml of 5% | 1.0 ml of 10% | 1.0 ml of 15% |

Study Part B: Exposure to Multiple Subcutaneous Rhamnolipid Injections

One week after completion of Study Part A, the subject injected himself with a total of 6 injections of 0.5 ml of a 15% solution of rhamnolipids. These injections were placed into the subcutaneous fat tissues of the subject's right lumbar region of his abdomen and his left iliac region on Day 1 of Study Part B. Each injection site was separated by approximately 1-2 inches. Over the next 10 days post-injection, a hardening of the injected subcutaneous fatty tissue along with a subsequent reduction in overall volume of the underlying fatty tissues was observed.

During this study, the subject showed a reduction in blood pressure. Prior to the rhamnolipid injections, the subject's typical blood pressure was, on average, approximately 135/85 mmHg (systolic/diastolic) while taking his prescribed anti-hypertensive medications (once daily 50 mg metoprolol and once daily 25 mg hydrochlorothiazide). However, on Day 3, the subject's blood pressure was reduced to approximately 110/65 mmHg while the subject was still taking his anti-hypertensive medications as prescribed. On Day 4, the subject discontinued taking his metoprolol medication, and his blood pressure remained, on average, around 110/65 mmHg. On Day 5, the subject discontinued taking his hydrochlorothiazide medication. On Day 8, the subject injected himself with an additional series of 6 injections of 0.5 ml of a 15% solution of rhamnolipids into the subcutaneous fat tissues of his right lumbar region of his anterior abdomen and his left iliac region. The subject's blood pressure remained within a range of 110/67 mmHg to 132/80 mmHg from Day 8 to Day 14. On Day 15, the subject's blood pressure started to rise to values of 145/82 mmHg to 155/85 mmHg, which were similar to the values seen prior to treatment.

Additionally, over the course of these studies, which lasted approximately 8 weeks, the subject's body weight decreased from 108 to 98.5 kg (BMI 27.1). There were no dietary restrictions for the subject during this study.

Figure 2:
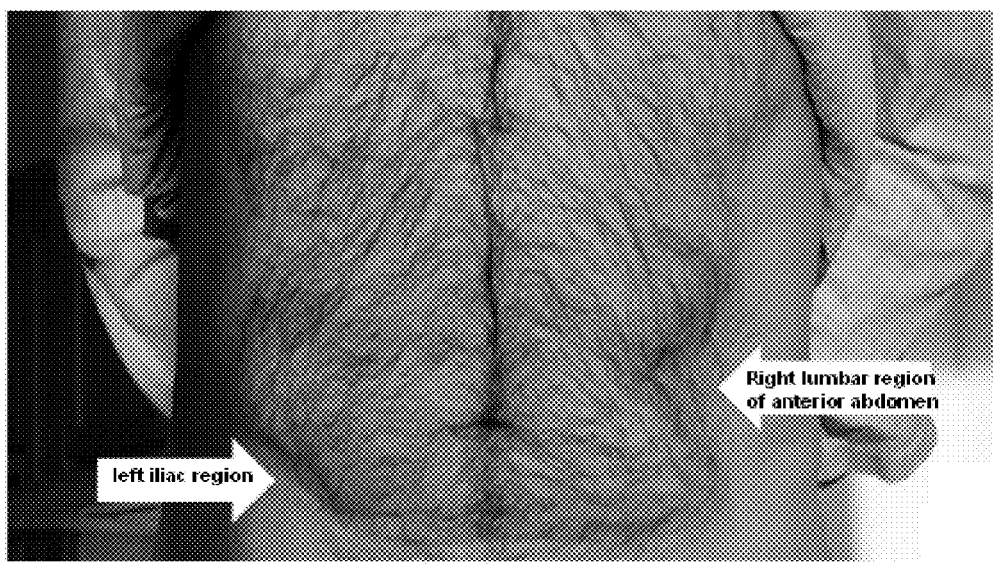
FIG. 2 is a mirror image photograph of the subject illustrating the visual decrease in localized fat observed following subcutaneous injections with rhamnolipids. The white arrow on the left indicates the subject's left iliac region injection site and the white arrow on the right indicates the subject's right lumbar region of anterior abdomen injection site.

A mirror image photograph of the subject illustrates the exemplary results achieved in this study (FIG. 2). The white arrows located on the left and right side of the photograph identify the injection sites on the subject's left iliac region and right lumbar region of his anterior abdomen. No scarring, skin deformation, or painful knots under the skin was observed at any of the subject's injection sites.

Conclusion

The results of this study demonstrate that subcutaneous injections with rhamnolipids, specifically, a combination of mono-rhamnolipid and di-rhamnolipid, resulted in a visual reduction of fat deposits and overall body weight in a human subject. These results provide evidence to suggest that rhamnolipids can be used for the treatment of unwanted localized fat deposits in patients. Additionally, the reduction of subcutaneous fatty tissue at the rhamnolipid injection sites accompanied by local tolerability suggests that the increased intracutaneous fat protrusion observed in cellulite can be reduced through intracutaneous and subcutaneous local injections of rhamnolipids. Furthermore, the concurrent decrease seen in the subject's blood pressure suggests that rhamnolipids can be used to treat hypertension.

Example 3

Objective

The objective of this study was to determine the effects of different treatment intervals and prolonged exposure of rhamnolipids on body weight and parameters of metabolic syndrome in rats.

Materials

Animal:

Five obese Zucker rats (Charles River Laboratories International, Inc. (Wilmington, Mass.), approximately 8 weeks old, were used in this study.

Rhamnolipids:

RPI-100 was used in this study.

Saline was used as a placebo for this study.

Methods

Figure 3:
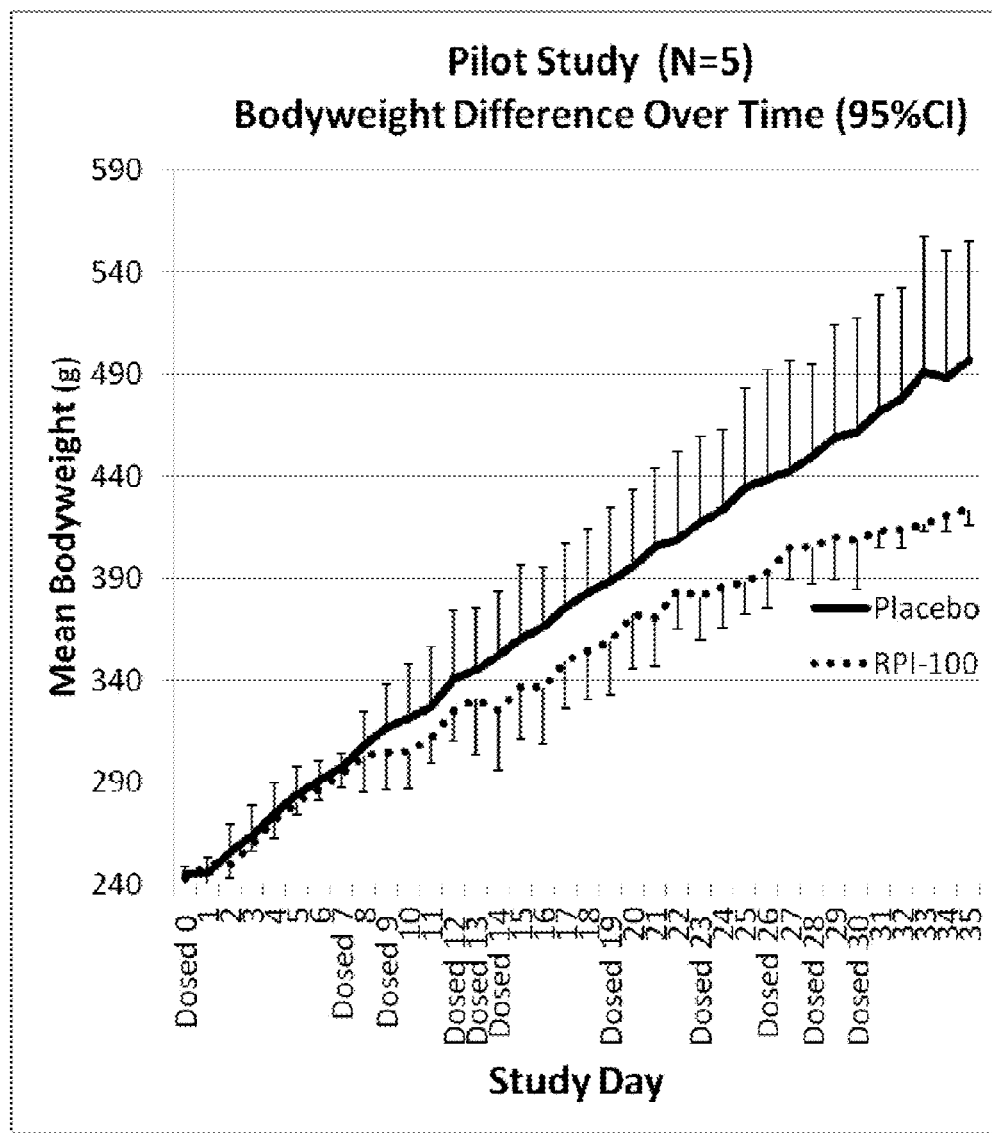
FIG. 3 shows the mean body weight (grams) of the rats treated with RPI-100 or the placebo. Body weight was measured on each day of the study (Study Day). Mean body weights were calculated and plotted for the groups treated with the placebo (black line) or RPI-100 (black dots). Rats were treated with either RPI-100 or the placebo on Study Days 0, 7, 9, 12, 13, 14, 19, 23, 26, 28, and 30 (Dosed).
Figure 4:
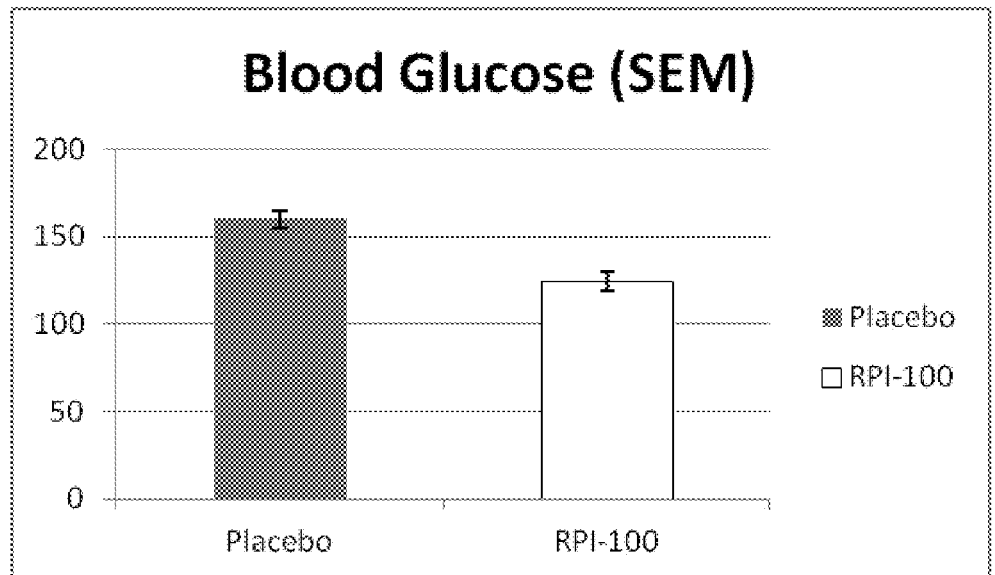
FIG. 4 shows mean blood glucose levels (SEM) of the placebo (grey bar) and RPI-100 (white bar) treated rats.
Figure 5:
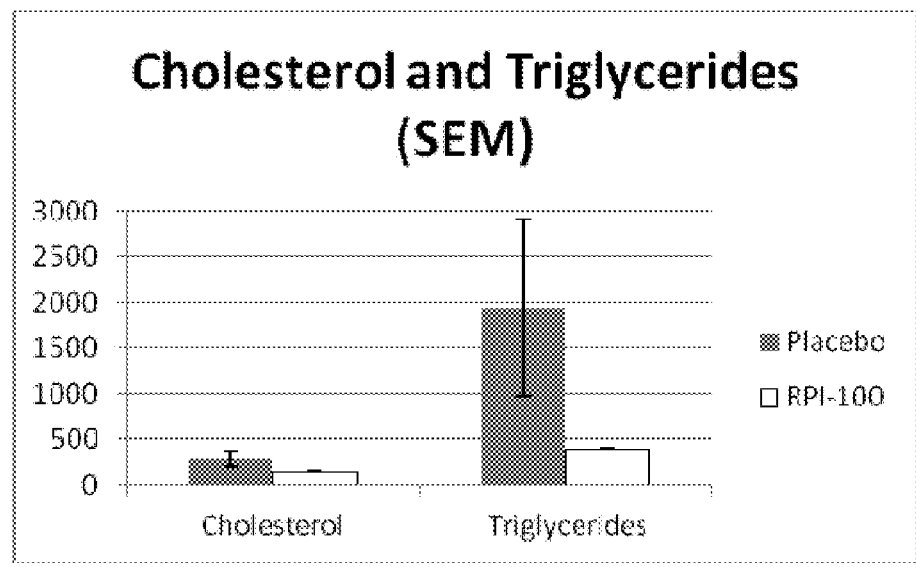
FIG. 5 shows mean cholesterol (left) and triglyceride (right) levels of the placebo (grey bar) and RPI-100 (white bar) treated rats.

Three rats were treated with interval, subcutaneous injections of RPI-100, while two rats were injected with a placebo. Fixed doses (120 mg/kg body weight) were administered as two 60 mg/kg injections into dorsal fat regions of the rats on a total of 11 days (Study Day 0, 7, 9, 12, 13, 14, 19, 23, 26, 28, 30) (FIG. 3). The sites of injections were alternated with each dose administration. Blood glucose, cholesterol, and triglyceride levels were measured on Day 39, which was 9 days after the last injection of RPI-100 (FIGS. 4-5). Renal biopsies were taken upon necropsy on Day 39 and histology findings analyzed (Table 2). All clinical assessments were performed by Quality Veterinary Laboratory, LLC. (Davis, Calif.). Animals were not fasted prior to clinical laboratory and necropsy assessments. Body weights of the rats were measured at the beginning of each day and recorded (FIG. 3).

Results

As demonstrated in FIG. 3, subcutaneous injections with RPI-100 were associated with a significant decrease in body weight gain on Day 35 (5 days after the last day of dosing) (two-tailed P value=0.0480 (unpaired t-test)). Additionally, rats treated with RPI-100 showed a decrease in blood glucose, triglyceride and cholesterol levels on Day 39 (9 days after the last day of dosing) compared with rats that were injected with the placebo (FIGS. 4-5). The graph presented in FIG. 4 indicates that the differences seen in blood glucose levels between the RPI-100 and placebo group are statistically significant because the 95% CI bars from the rat group treated with RPI-100 do not overlap with the bars from the group treated with the placebo (P value=0.0349 (unpaired t-test)). Finally, the rats that received the placebo presented with initial histological signs consistent with diabetic renal damage, whereas the rats that received the RPI-100 did not show significant lesions (Table 2).

TABLE 2

Renal Histology

| Group | Animal | Kidney Histology |
|---|---|---|
| Placebo | 101 | Renal tubular dilation, mild, multifocal |
|  | 102 | Renal tubular dilation and basophilia, moderate, multifocal |
| RPI-100 | 201 | NSL (No significant lesions) |
|  | 202 | NSL |
|  | 203 | NSL |

Conclusion

This pilot study demonstrates that interval injections with RPI-100 in a rat model were associated with a statistically significant difference in body weight gain. This result was concomitant with improvements in parameters of metabolic syndrome, such as blood glucose, cholesterol, and triglyceride levels compared to rats that received the placebo. These results suggest that rhamnolipids can be used for the treatment of metabolic syndrome and type 2 diabetes. In addition, the rats that received the placebo presented with initial histological signs of renal damage in contrast to the rats that received RPI-100, which suggests that rhamnolipids can be used to treat type 2 diabetes, obesity-related kidney disease, and glomerulosclerosis.

Example 4

Objective

The objective of this study was to use a larger population of rats to confirm the consistent and rapid reduction of body weight gain observed upon treatment with rhamnolipids as seen in the pilot study presented in Example 3, and to further assess effects on parameters of metabolic syndrome, non-alcoholic fatty liver disease and renal disease.

Materials

Animals:

Fifteen obese Zucker rats (Harlan Laboratories (Livermore, Calif.)), approximately 8 weeks old, were used in this study.

Rhamnolipids:

RPI-100 was used in this study.

Saline was used as a placebo in this study.

Methods

Figure 6:
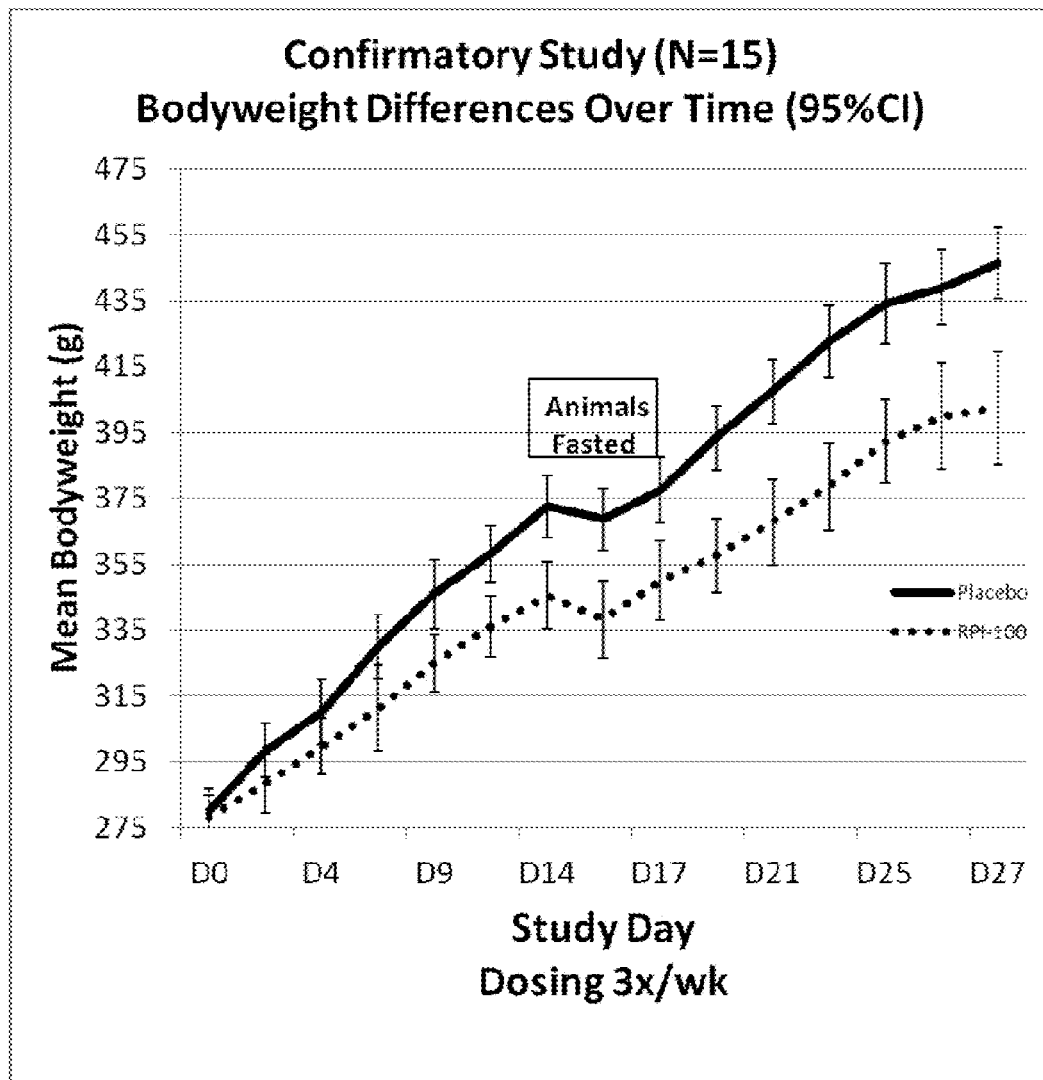
FIG. 6 shows the plotted mean body weight (grams) of the rats treated with RPI-100 or the placebo. Rats were treated with either RPI-100 or the placebo three times per week. Body weight was measured on each day of dose administration. Mean body weights were calculated and plotted for the groups treated with the placebo (black line) or RPI-100 (black dots). Rats were fasted from Day 14-15.
Figure 8:
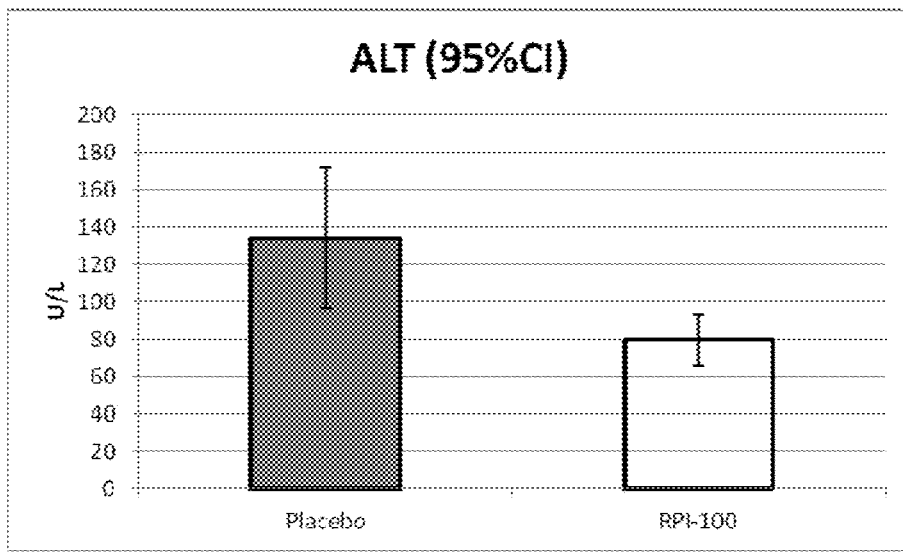
FIG. 8 shows mean alanine aminotransaminase (ALT) levels (U/L of the placebo (grey bar) and RPI-100 (white bar) treated rats.
Figure 9:
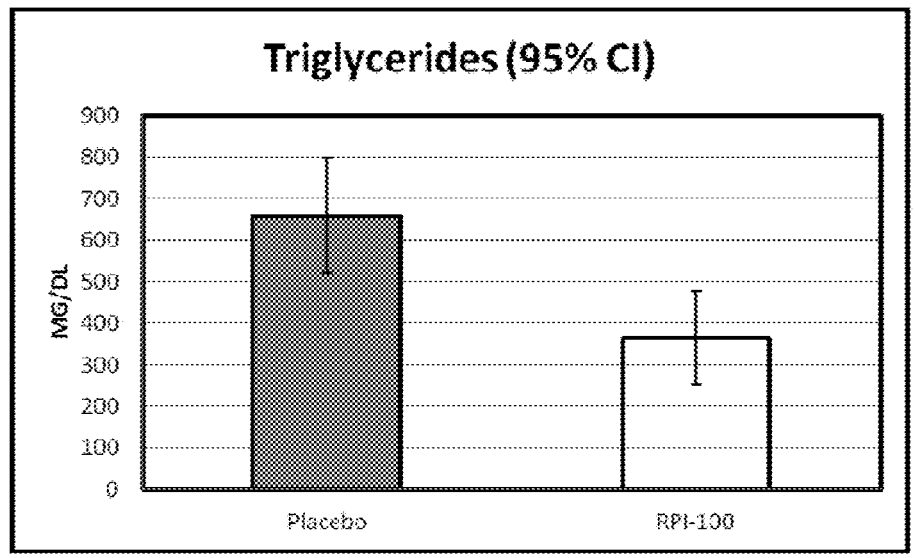
FIG. 9 shows mean triglyceride levels (MG/DL) of the placebo (grey bar) and RPI-100 (white bar) treated rats.
Figure 10:
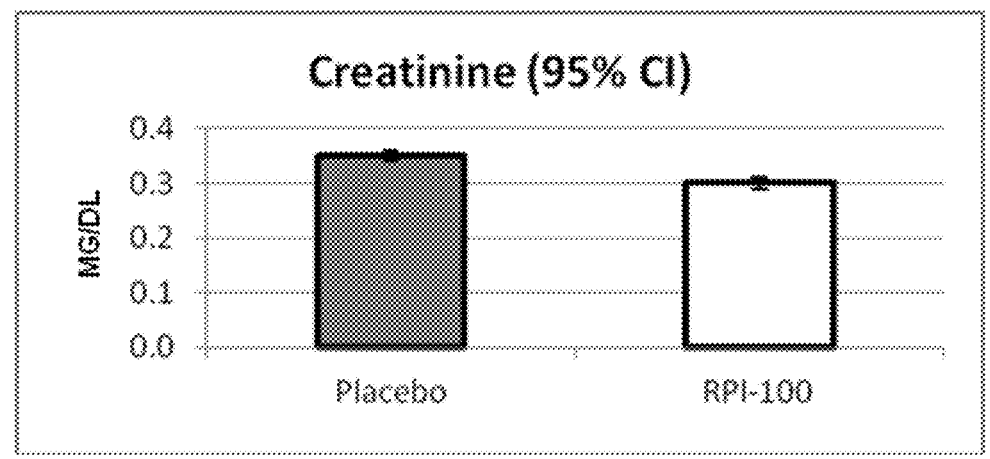
FIG. 10 shows mean creatinine levels (MG/DL) of the placebo (grey bar) and RPI-100 (white bar) treated rats.

In this study, seven rats received RPI-100 and eight rats received the placebo. Fixed doses (120 mg/kg body weight) of RPI-100 were administered as two 60 mg/kg subcutaneous injections into dorsal fat regions of the rats. Injections were administered three days a week for 4 weeks (Days 0-27) (FIG. 6). The injection sites were alternated with each dose administration. Clinical laboratory assessments were performed on the third day after the last dose administration (Day 30) (FIGS. 8-10). Animals were provided ad libetum access to chow, except on Days 14-15 when they were fasted. Animals were not fasted prior to clinical safety and hematological laboratory assessments, which were performed on Day 30. Body weights of the rats were measured and recorded on each day that RPI-100 was administered (FIG. 6). All clinical assessments were performed by Quality Veterinary Laboratory, LLC. (Davis, Calif.).

Results

Rats that were administered interval injections with RPI-100 showed a statistically significant difference in body weight from Day 9 through Day 27 (last day of dosing) (FIG. 6). The P values were <0.05 for the unpaired t-tests comparing body weight differences between RPI-100 and placebo treated groups for Study Days 9 through 27 (Table 3).

TABLE 3

P-Values (Unpaired T-Tests) Comparing Body Weight Differences over Time for RPI-100 and Placebo Treated Groups

| Study Day | P value |
|---|---|
| Day 9 | 0.0137 |
| Day 11 | 0.0056 |
| Day 14 | 0.0027 |
| Day 16 | 0.0018 |
| Day 17 | 0.0003 |
| Day 19 | 0.0005 |
| Day 21 | 0.0004 |
| Day 23 | 0.0003 |
| Day 25 | 0.0006 |
| Day 26 | 0.0021 |
| Day 27 | 0.0009 |

Figure 7:
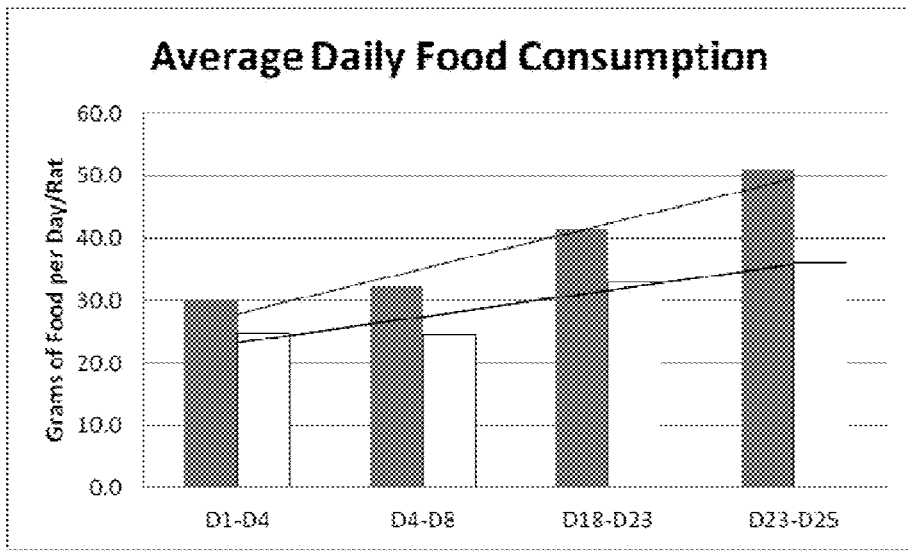
FIG. 7 shows average daily food consumption for the placebo (grey bars) and RPI-100 (white bars) treated rats. The average daily food consumption was calculated by measuring the total amount of food consumed (grams) per rat during a specified time period (Day 1-4, Day 4-8, Day 18-23, Day 23-25).

Additionally, average food consumption of the rats treated with RPI-100 was reduced compared with placebo treated rats (FIG. 7). A statistically significant difference was observed in total food consumption measured between Days 1-25 (P=0.0407 (unpaired t-test)).

Liver transaminase levels, specifically alanine aminotransaminases (ALT), are indicators of non-alcoholic fatty liver disease and were decreased (improved) in animals treated with RPI-100 (FIG. 8) (ALT P value=0.0261 (unpaired t-test)). Triglyceride values, excluding one outlier with the greatest value from each treatment group, were significantly decreased in the RPI-100 treated rats compared with the placebo treated rats (FIG. 9) (triglyceride P value=0.0228 (unpaired t-test)). Finally, creatinine levels, which are an indicator of renal function that increase during renal failure, were significantly reduced in animals treated with RPI-100 as indicated by the 95% CI bars (FIG. 10) (creatinine P value=0.0285 (unpaired t-test)). No significant differences in red or white blood cell counts, or hematocrit were observed.

Conclusion

The results in this study showed a significant reduction of body weight gain upon treatment with RPI-100 in obese Zucker rats, which indicates that rhamnolipids can be used for treating obesity. Additionally, this study also demonstrates that rhamnolipids can be used to treat metabolic syndrome because the rats treated with RPI-100 showed significant improvements in triglyceride levels. These favorable effects on metabolic syndrome are further supported by the observations seen in previous examples showing that blood pressure was improved in a pre-obese individual (Example 2) and that blood glucose levels were significantly reduced in obese Zucker rats (Example 3) following treatment with rhamnolipids.

Obese Zucker rats are predisposed to developing non-alcoholic fatty liver disease and obesity-related kidney disease, and ALT levels are an important parameter in non-alcoholic fatty liver disease. Therefore, the decrease seen in ALT values in obese Zucker rats treated with RPI-100 shows that rhamnolipids can be of utility to treat non-alcoholic fatty liver disease and non-alcoholic steatohepatitis (NASH). Finally, as creatinine levels are an important parameter in obesity-related kidney disease, the results demonstrate that rhamnolipids can also be used to treat obesity-related kidney disease and glomerulosclerosis because rats treated with RPI-100 showed a statistically significant decrease in creatinine values compared with those that received the placebo.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude the specification.

What is claimed is:

1. A method for reducing excessive body weight from a mammal subject suffering from excessive weight or overt obesity, comprising the steps of identifying a subject suffering from excessive weight or overt obesity, and administering to the subject an effective amount of rhamnolipids, wherein said rhamnolipids are selected from the group consisting of: $\alpha$-L-rhamnosyl-$\beta$-hydroxydecanoyl-$\beta$-hydroxydecanoate, $\alpha$-L-rhamnosyl-(1,2)-$\alpha$-L-rhamnosyl-$\beta$-hydroxydecanoyl-$\beta$-hydroxydecanoate, $\alpha$-L-rhamnopyranosyl-(1,2)-$\alpha$-L-rhamnopyranosyl-$\beta$-hydroxydecanoyl-$\beta$-hydroxydodecanoate; $\alpha$-L-rhamnopyranosyl-(1,2)-$\alpha$-L-rhamnopyranosyl-$\beta$-hydroxytetradecanoyl-$\beta$-hydroxytetradecanoate, or a combination thereof.

2. The method according to claim 1, for reducing excessive body weight from a mammal suffering from overt obesity.

3. The method according to claim 2, wherein said rhamnolipids are $\alpha$-L-rhamnosyl-$\beta$-hydroxydecanoyl-$\beta$-hydroxydecanoate, $\alpha$-L-rhamnosyl-(1,2)-$\alpha$-L-rhamnosyl-$\beta$-hydroxydecanoyl-$\beta$-hydroxydecanoate, or the combination thereof.

4. The method according to claim 2, wherein said rhamnolipids are in a form suitable for oral, intranasal, subcutaneous, percutaneous, intracutaneous, or intravenous administration.

5. A method for treating an obesity-related condition in a subject, comprising the steps of:
identifying a subject suffering from (i) excessive body weight or overt obesity, and (ii) an obesity-related condition, and
administering to the subject an effective amount of rhamnolipids, wherein said obesity-related condition is metabolic syndrome, type 2 diabetes, non-alcoholic steatohepatitis, or non-alcoholic fatty liver disease, and said rhamnolipids are selected from the group consisting of: $\alpha$-L-rhamnosyl-$\beta$-hydroxydecanoyl-$\beta$-hydroxydecanoate, $\alpha$-L-rhamnosyl-(1,2)-$\alpha$-L-rhamnosyl-$\beta$-hydroxydecanoyl-$\beta$-hydroxydecanoate, $\alpha$-L-rhamnopyranosyl-(1,2)-$\alpha$-L-rhamnopyranosyl-$\beta$-hydroxydecanoyl-$\beta$-hydroxydodecanoate; $\alpha$-L-rhamnopyranosyl-(1,2)-$\alpha$-L-rhamnopyranosyl-$\beta$-hydroxytetradecanoyl-$\beta$-hydroxytetradecanoate, or a combination thereof.

6. The method according to claim 5, wherein said obesity-related condition is metabolic syndrome.

7. The method according to claim 5, wherein said rhamnolipids are $\alpha$-L-rhamnosyl-$\beta$-hydroxydecanoyl-$\beta$-hydroxydecanoate, $\alpha$-L-rhamnosyl-(1,2)-$\alpha$-L-rhamnosyl-$\beta$-hydroxydecanoyl-$\beta$-hydroxydecanoate, or the combination thereof.

8. The method according to claim 5, wherein said rhamnolipids are in a form suitable for oral, intranasal, subcutaneous, percutaneous, intracutaneous, or intravenous administration.

* * * * *